United States Patent [19]
Bowdler

[11] Patent Number: 5,131,116
[45] Date of Patent: Jul. 21, 1992

[54] EXTENSION HANDLE FOR A SEAT ADJUSTMENT LEVER

[76] Inventor: Shirley Bowdler, 1792 Geiberger Dr., Fayetteville, N.C. 28303

[21] Appl. No.: 736,789

[22] Filed: Jul. 29, 1991

[51] Int. Cl.⁵ .............. A47B 95/02; A47C 15/00; B25G 1/04
[52] U.S. Cl. .................. 16/114 R; 16/DIG. 25; 297/463
[58] Field of Search ............. 16/114 R, 115, DIG. 25; 297/463

[56] References Cited

U.S. PATENT DOCUMENTS

| | | | |
|---|---|---|---|
| 757,195 | 4/1904 | Huff | 16/114 R |
| 2,244,585 | 6/1941 | Tweit | 16/114 R |
| 4,683,610 | 8/1987 | Richards et al. | 16/DIG. 25 |

FOREIGN PATENT DOCUMENTS 78128  9/1919  Austria ................. 16/114 R

Primary Examiner—Robert L. Spruill
Assistant Examiner—Carmine Cuda
Attorney, Agent, or Firm—Rhodes, Coats & Bennett

[57] ABSTRACT

An extension handle for a seat adjustment lever enables physically handicapped persons to more easily adjust their car seat. The extension handle includes an extension bar having a lower end portion and an upper end portion terminating in a handle grip. A connecting block is secured to the lower end portion of the extension bar and is adapted to be mounted on the seat adjustment lever. The extension bar is bent so that it extends upwardly towards the top of the top of the seat where it can more easily reached by physically handicapped persons. The extension bar also provides additional leverage which makes the seat adjustment lever more easily to operate.

7 Claims, 4 Drawing Sheets

EXTENSION HANDLE FOR A SEAT ADJUSTMENT LEVER

FIELD OF THE INVENTION

The present invention relates generally to automotive accessories for adapting conventional automobiles for use by physically handicapped persons, and more particularly to an attachment for a seat adjustment mechanism.

BACKGROUND OF THE INVENTION

In most automobiles, the front seats are mounted on a seat track assembly which allows the seat to be selectively moved forwardly and rearwardly. The seat track assembly includes a latching mechanism which allows the seat to be secured at a selected position. A seat adjustment lever is operatively connected with the latching mechanism for disengaging the latching mechanism thereby enabling the seat to be moved back and forth along the tracks.

In most cars, the seat adjustment lever is located well below the seat where it can be difficult to reach, particularly for physically handicapped persons, persons suffering from arthritis, or other individuals with similar impairments. Some physically impaired persons may also find it difficult to manipulate the seat adjustment lever even when it can be reached. Cars having electrically operated seats tend to be more expensive than other cars. Many handicapped or physically impaired persons cannot afford these more expensive vehicles.

For the foregoing reasons, there is a need for a device which gives handicapped and physically impaired persons easier access to the seat adjustment lever, and for a device which makes operation of the seat adjustment lever more manageable.

SUMMARY AND OBJECTS OF THE INVENTION

The present invention is an extension handle which can be secured to a seat adjustment lever on a car seat to adapt the seat adjustment lever for use by handicapped and physically impaired persons. The extension handle can be secured to most seat adjustment levers without modification in only a few minutes.

The extension handle includes an extension bar having an upper end and a lower end. A clamping means is provided for clamping the lower end of the extension bar to the seat adjustment lever. The clamping means includes a flexible band which extends around the seat adjustment lever, and tightening means for tightening the flexible band around the seat adjustment lever. More particularly, the flexible band includes a plurality of longitudinally spaced, transversely extending slots. The tightening means includes a screw having threads engaged with the slots in the flexible band.

Accordingly, it is a primary object of the present invention to provide an extension handle for a seat adjustment lever for a car seat to bring the adjustment mechanism within their reach.

Another object of the present invention is to provide an extension handle for a seat adjustment lever to make the seat adjustment mechanism easier to operate.

Another object of the present invention is to provide an extension handle for a seat adjustment lever which can be easily and quickly secured to an existing seat adjustment lever in an automobile.

Other objects and advantages of the present invention will become apparent and obvious from a study of the following description and the accompanying drawings which are merely illustrative of such invention.

DETAILED DESCRIPTION OF THE INVENTION

Figure 1:
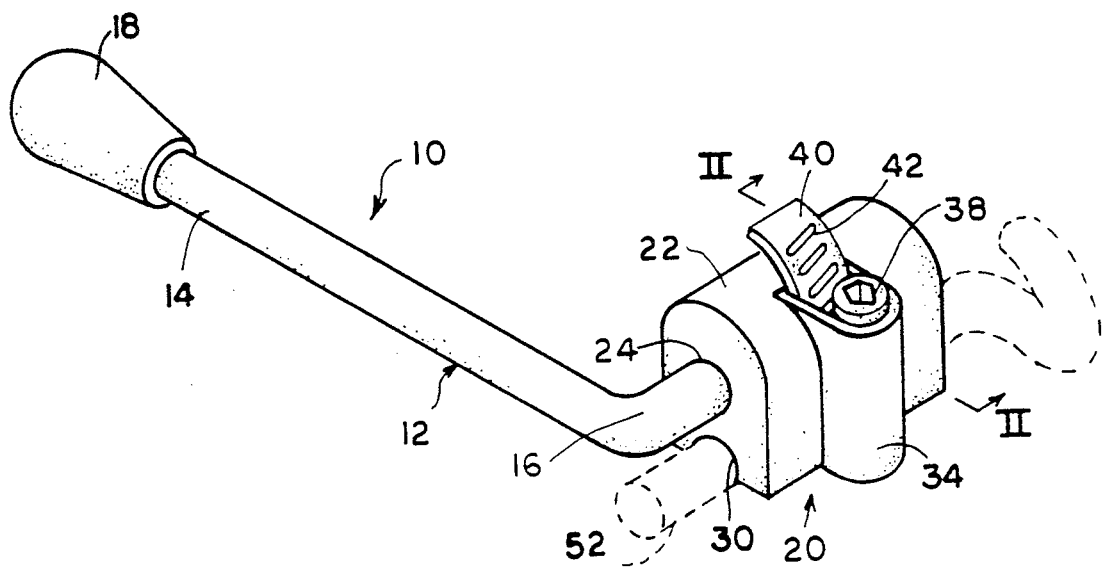
FIG. 1 is a perspective view of the extension handle of the present invention.

Referring now to the drawings, and particularly to FIG. 1, the extension handle of the present invention is shown therein and indicated generally by the numeral 10. The extension handle includes an extension bar indicated generally at 12 and a connecting means 20 for securing the extension bar 12 to a seat adjustment lever 52 shown in dotted lines in FIG. 1.

The extension bar 12 includes an upper end portion 14 and a lower end portion 16. The extension bar 12 is bent approximately ⅓ the distance from the lower end to the upper end. Thus, the upper end portion 14 extends upwardly at an angle towards the top of the seat. A knob or grip 18 is secured at the terminal end of the upper end portion 14.

The connecting means 20 is adapted to receive the lower end portion 16 of the extension bar 12 and to mount it to the seat adjustment lever 52 of the car seat 50. The connecting means 20 includes a generally barrel shaped connected block 22. A longitudinally extending opening 24 is formed in the connecting block 22 for receiving the lower end portion 16 of the extension bar 12. The extension bar 12 is secured in the opening 24 of the connecting block 22 by means of a set screw 28. The set screw 28 is threaded into a set screw hole 26 which intersects the longitudinal opening 24.

The connecting block 22 also includes a semi-circular groove 30 which extends parallel to the longitudinal opening 24. The groove 30 is sized to receive the seat adjustment lever 52. A band clamp 32 secures the seat adjustment lever within the groove 30.

Figure 2:
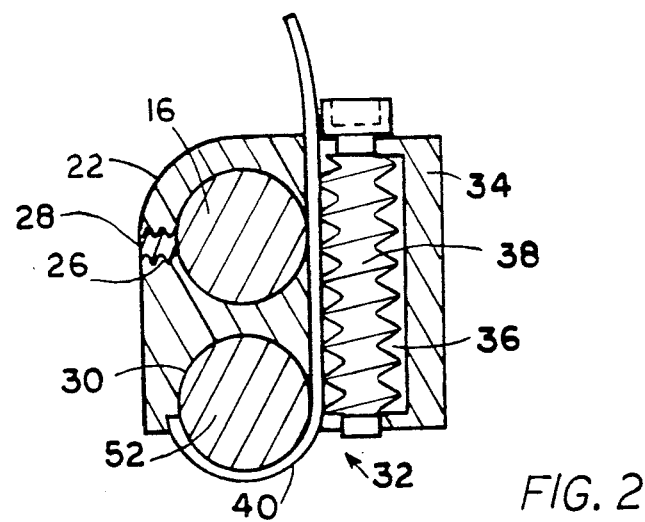
FIG. 2 is a section view thereof taken through line II—II of FIG. 1.
Figure 3:
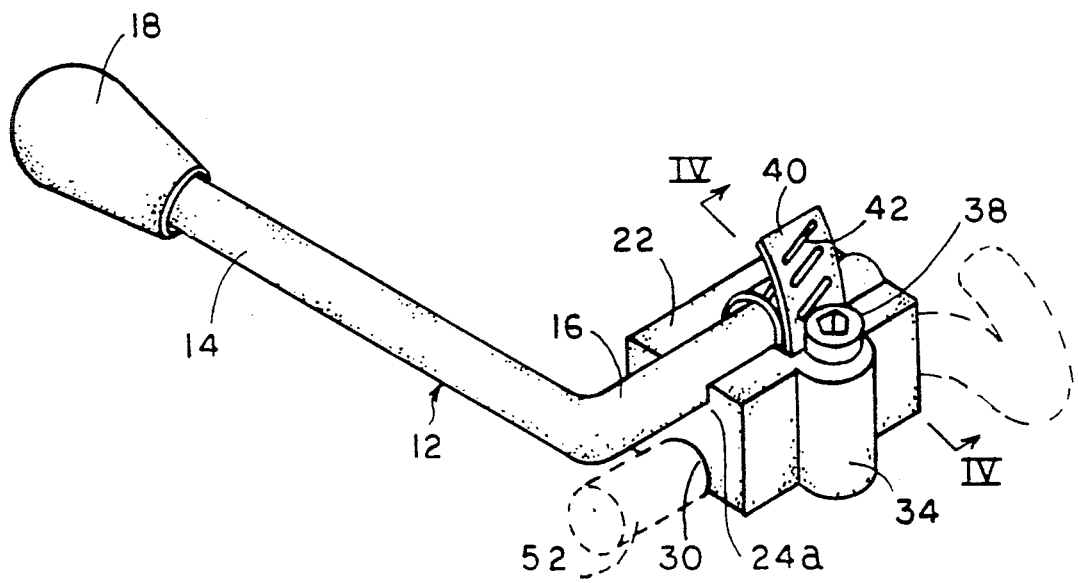
FIG. 3 is a perspective view of a second embodiment of the extension handle.

The band clamp 32 comprises a flexible band 40 which extends around the seat adjustment lever and a screw 38 for tightening the flexible band 40. The screw 38 is rotatably journaled in a screw mounting column 34 attached to one side of the connecting block. The screw column 34 defines a cavity 36 which houses the shank of the screw. The flexible band, which is fixedly secured at one end to the connecting block 22, extends around the seat adjustment lever and upwardly through the cavity 36 in the screw column 34. The flexible band 40 includes a plurality of longitudinally spaced, transversely extending slots 42 which are engaged by the threads of the screw 38 as best seen in FIG. 2. Thus, the flexible band 40 can be tightened or loosened by simply turning the screw 38.

To use the extension handle 10 of the present invention, the extension bar 12 is inserted into the connecting block 22 and is securely fastened by tightening set screw 28 against the extension bar 12. The connecting block is then mounted on the seat adjustment lever 52 by passing the end of the seat adjustment lever 52 between the groove 30 and the flexible band 40. The adjustment screw 38 is then turned clockwise to tighten the flexible band 40 around the seat adjustment lever 52. The relatively large surface area of the groove 30 in combination with the force of the band clamp 32 provides a secure connection between the extension handle 10 and the seat adjustment lever 52. While one band clamp 32 will generally be enough to secure the extension handle 10 to the seat adjustment lever 52, it will be readily appreciated that more than one band clamp can be used as needed.

Figure 4:
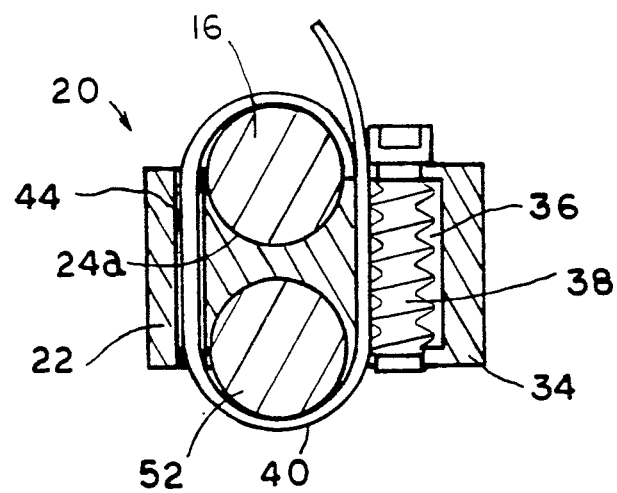
FIG. 4 is a section view thereof taken through line IV—IV of FIG. 3.
Figure 5:
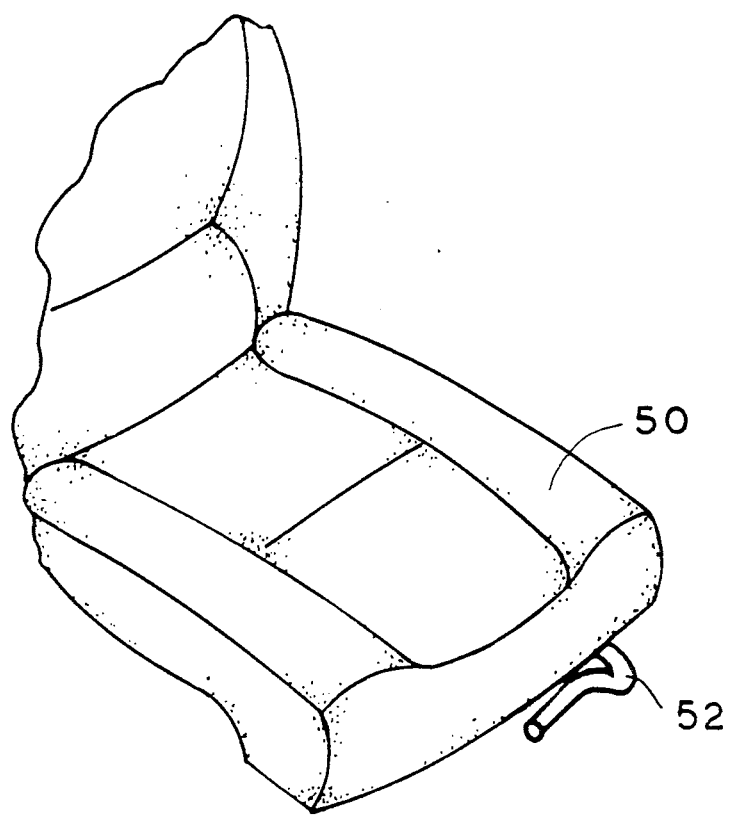
FIG. 5 is a partial perspective of a car seat showing a conventional seat adjustment lever.
Figure 6:
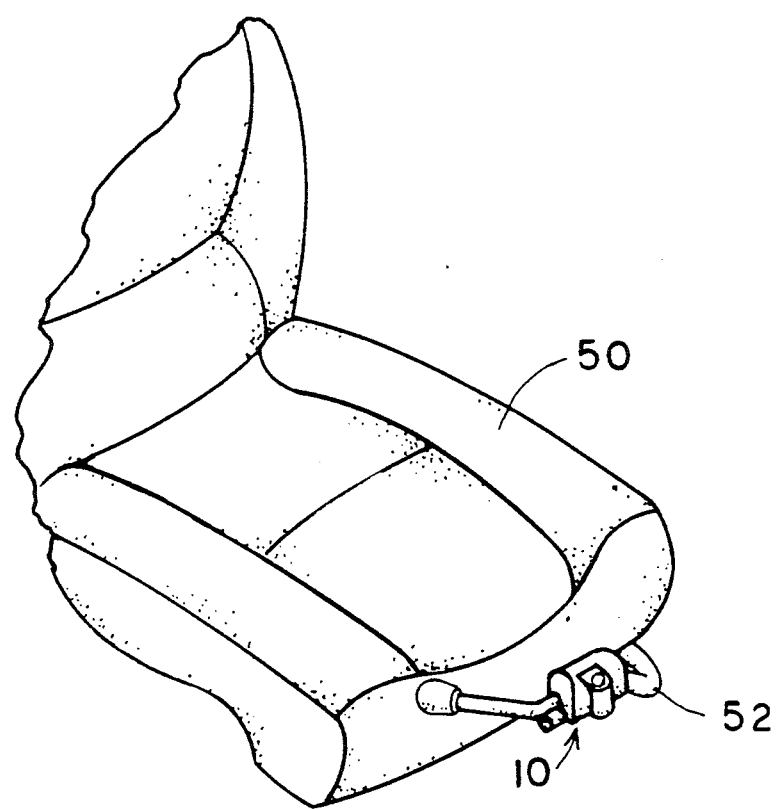
FIG. 6 is a perspective view of a car seat with the extension handle of the present invention attached to the seat adjustment lever.

Referring now to FIG. 4, a second embodiment of the present invention is shown. The second embodiment is similar in most respects to the first embodiment. Accordingly, the same reference numerals used in connection with the first embodiment have been used with the second embodiment to designate similar components.

Turning now to the second embodiment, the same includes an extension bar indicated generally at 12 and a connecting means indicated generally at 20. The extension bar 12 is identical in all respects to the first embodiment. Accordingly, further description of the extension bar 12 is omitted. Reference can be made to earlier portions of this specification for a more complete description.

The connecting means 20 is also similar to the first embodiment in that it includes a connecting block indicated generally at 22 and a band clamp 32 for securing the extension bar 12 to the seat adjustment lever 52. However, the form of the connecting block 22 is somewhat different than the first embodiment. In particular, the connecting block 22 of the second embodiment is generally rectangular in form and includes semi-circular grooves 24a and 30 in the top and bottom surfaces respectively. The groove 24a in the top surface is adapted to receive the lower end portion 16 of the extension bar 12. The groove 30 in the bottom surface of the connecting block 22 is adapted to receive the seat adjustment lever 52. Both the extension bar 12 and seat adjustment lever are secured in their respective grooves by a single band clamp 32. The flexible band 40 is fixed at one end to the top of the connecting block 22. The band extends around and over the lower end portion 16 of the extension bar 12 and passes downwardly through a transverse opening 44 in the connecting block 22. The band 40 then passes around the underside of the seat adjustment lever 52 and extends upwardly through the cavity 36 in the screw support column 34. The adjustment screw 38 engages the band. More particularly, the threads of the screw 38 engage with the slots 42 in the band. Thus, when the screw is turned clockwise, the band will be tightened around the extension bar 12 and the seat adjustment lever 52.

The extension handle 10 of the second embodiment is used in the same manner as the previous embodiment. The lower end portion of the extension bar and the seat adjustment lever are inserted into grooves 24a and 30 respectively. The adjustment screw 38 is then turned clockwise to tighten the band 40 around the extension bar 12 and seat adjustment lever 52 to secure the handle 10 to the seat adjustment lever 52. From the foregoing, it is apparent that the present invention is more easily accessible to handicapped persons since it effectively brings the handle closer to the top of the car seat 50. Further, the extension handle 10 of the present invention provides greater leverage making it easier to manipulate the seat adjustment lever.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An extension handle for a seat adjustment lever comprising:
    a) an extension bar having an upper end portion and a lower end portion;
    b) an inflexible connecting block having means formed therein for receiving the lower end portion of the extension bar and for receiving the seat adjustment lever;
    c) means for securing the lower end of the extension bar to said connecting block; and
    d) means for securing the seat adjustment lever to said connecting block.

2. An extension handle for a seat adjustment lever comprising:
    a) an extension bar having an upper end and a lower end;
    b) a connecting block secured to the lower end of the extension bar for securing the extension bar to the seat adjustment lever, the connecting block including an elongated, semi-circular groove for engaging the seat adjustment lever;
    c) clamping means for securing the seat adjustment lever within the semi-circular groove, the clamping means including a flexible band for encircling the seat adjustment lever and having a plurality of longitudinally space, transversely extending slots; and
    d) means for tightening said flexible band around the seat adjustment lever, the means for tightening said flexible band including a screw having threads engaged with the slots in the flexible band.

3. An extension handle for a seat adjustment lever comprising:
    a) an extension bar having an upper end portion and a lower end portion;
    b) an inflexible connecting block having a first cavity for receiving the lower end portion of the extension bar, and a second cavity for receiving the seat adjustment lever;
    c) means for securing the lower end of the extension bar in the first cavity of the connecting block; and
    d) means for securing the seat adjustment lever in the second cavity of the connecting block.

4. The extension handle according to claim 3 wherein the first cavity comprises a longitudinal opening in the connecting block for receiving the lower end portion of the extension bar, and wherein the means for securing the lower end portion of the extension bar comprises a set screw threadably engaged in a transverse hole in the connecting block.

5. The extension handle according to claim 4 wherein the second cavity comprises a semi-circular groove formed in the connecting block and extending parallel to the longitudinal opening, and wherein the means for securing the seat adjustment lever comprises a flexible band for encircling the seat adjustment lever, and means for tightening the flexible band around the seat adjustment lever.

6. The extension handle according to claim 3 wherein the first and second cavities comprise a pair of semi-circular grooves formed in the top and bottom of the connecting block respectively, and wherein the lower end portion of the extension bar and the seat adjustment lever are secured in their respective grooves by a flexible band extending around both the lower end portion of the extension bar and the seat adjustment lever.

7. The seat adjustment lever according to claim 6 wherein the connecting block includes a pair of transverse openings disposed on laterally opposite sides of the longitudinal grooves in the connecting block, and wherein the flexible band passes through the transverse openings in the connecting block.

* * * * *